United States Patent [19]

Kékesi et al.

[11] Patent Number: 4,803,069
[45] Date of Patent: Feb. 7, 1989

[54] COMPOSITION FOR THE TREATMENT OF ACNE

[75] Inventors: Sándor Kékesi; Piroska Tamási; Veronika Pál; Sándor Jancsó; Ilona Kristóf née Szvitil; György Bacsa; Katalin Kovács née Hadady, all of Debrecen, Hungary

[73] Assignee: Biogál Gyógyszergyár, Debrecen, Hungary

[21] Appl. No.: 874,247

[22] Filed: Feb. 7, 1989

[30] Foreign Application Priority Data

Jun. 18, 1985 [HU] Hungary .................. 2389/85

[51] Int. Cl.$^4$ .................. A61K 7/45; A61K 7/075; A61K 35/78
[52] U.S. Cl. .................. 424/74; 424/195.1; 514/859
[58] Field of Search .................. 514/859, 864; 424/74, 424/195.1

[56] References Cited

U.S. PATENT DOCUMENTS

| 4,428,933 | 1/1984 | King .................. 424/93 |
| 4,446,145 | 5/1984 | Van Beves .................. 514/399 |
| 4,569,839 | 1/1986 | Grollier et al. .................. 424/74 |
| 4,614,652 | 9/1986 | Vályi et al. .................. 514/864 |

FOREIGN PATENT DOCUMENTS 209724 1/1987 European Pat. Off. .

Primary Examiner—Ellis P. Robinson
Assistant Examiner—Susan S. Rucker
Attorney, Agent, or Firm—Schweitzer & Cornman

[57] ABSTRACT

The invention relates to a composition suitable for the treatment of acne. The composition of the present invention comprises as active ingredient an extract of a plant, more particularly the extract of the rhizoma of wheat grass (*Graminis rhizoma*) optionally in admixture with the extract of other plants and antibacterial agents.

The cosmetical compositions of the present invention quickly make oily greasy acne skin relatively symptom-free, while iritating, allergic or light sensitizing side-effects are not observed.

6 Claims, No Drawings

COMPOSITION FOR THE TREATMENT OF ACNE

This invention relates to a composition for the treatment of acne and a process for the preparation thereof. More particularly it is concerned with a composition suitable for the treatment of the most common and wide-spread type of pathological skin processes caused by primary metabolism, namely for the treatment of seborrhoea, including various acne/blackhead, blister-/lesions.

Seborrhoea is a pathologcal process based on the increased and qualitatively modified function of the sebaceous glands of the skin which manifests itself in an increased production and change composition of skin sebum. The said increased sebum production makes the skin oily and greasy, while parakerathosis and various forms of desquamation appear. In addition to the above symptoms seborrhoea causes skin lesions accompanied by the hyperkerathosis of hair follicle vessels and the hair follicle vessels are clogged by thickened sebum. This symptom is called "comedo formation". It mainly occurs in humans on the face skin and the Arnozan-type triangle.

According to most recent theories endocrine system plays a role in the formation of seborrhoea and bacterial infection is already one of the characteristic consequences.

Acne contitutes a more or less serious manifestation of seborrhoea appearing in the puberty period.

At the beginning comedos are observed on the oily greasy skin. As characteristic symptom of juvenile acne a bacterial strain generally present—Cornybacterium acnes—has been identified. According to Hungarian Pat. No. 171,517 an oral composition is proposed for the treatment of the symptom, the said composition comprising lyophylized strains of inactived Cornybacterium acnes. In the said patent specification an agent based on active immunity is disclosed for the treatment.

It is known for a long time that young individuals suffering from various forms of acne get into unfavourable social position due to the rude and striking changes of the face. There are also known various methods for the alleviation or termination of the said disease or at least the symptoms thereof. Milder forms of acne vulgaris respond in the desired manner to suitable local treatment when a diet enriched in vegetable components and vitamins but having a reduced fat and carbohydrate content is applied. Ih such cases treatment of the affected skin surface with ointments and shaking mixtures comprising sulfur ichthiol and optionally salicylate is often suggested in combination with lukewarm compress having disinfecting effect. Sulfur containing compounds, cysteine derivatives are proposed in German patent publications Nos. 1,908,574, 1.918,907 and 2,620,850 and U.S. Pat. No. 4,428,933. Composititons disclosed in the latter U.S. patent comprise in addition to generally known sulfur containing and peroxide compounds also substances of natural origin (e.g. mustard seed, oatmeal, yeast and egg-yolk).

In the present patent specification orally administered compositions suitable for the treatment of acne are not discussed in details but local agents and compositions are set forth below.

Local compositions are frequently applied which utilize a characteristic feature of the symtoms, namely that Corynebacterium acnes—being a characteristic component of comedos—prefers anaerobic environment. Accordingly the use of azo derivatives and peroxides temporarily terminates the characteristic features of the clinical pattern. In several cases the said compounds producing a local environment enriched in oxygen are combined with antibacterial agents and often synergism is observed. The use of the above compositions is based on the recognition that peroxides inhibit the formation of extracellular lypase while antibiotics inhibit the propagation of lypase producing bacteria /C. acnes/. Compositions utilizing the above theory are disclosed in British patent specifications Nos. 1,539,771, 2,088,717 and 2,090,135; U.S. patent specification No. 4,446,145; French patent specification No. 2,383,667; German patent publication No. 2,918,943; and PCT patent application No. 83/628.

According to a further group of patent specifications compositions comprising as primary component antibiotic are disclosed. Antibiotics most widespreadly used fot the treatment of acne are penicillin and erythromycin (British patent specification No. 1,587,428 and U.S. patent specification No. 4,261,962) tetracycline, neomycin (British patent specification No. 1,054,124), clindamycin, lincomycin and griseofulvin (DOS No. 2,557,431; European patent applications Nos. 52,705 and 52,404) are also suitable for this purpose.

Several attempts were made to elaborate a complex creme and ointment for the treatment of acne comprising as active ingredient a plant extract of natural origin either per se or in admixture with further active ingredients, particularly antibiotics.

The composition disclosed in European patent application No. 41,030 comprising the alkaloids of vinca rosea in admixture with an adjuvant facilitating penetration. According to Hungarian patent application Ser. No. 3213/82 drogues extracted with fruit-brandy are used as active ingredient of anti-acne composition in admixture with sulfur containing compounds (ichthiol).

The use of the said composition is however often accompanied by irritating, light sensitizing and also allergenic effect. Composition comprising sulfur containing compounds and rigorously acting peroxides often caused desquamation of the skin which may serve as a source of further infection It is the object of the present invention to provide a composition which provides the change of the characteristic clinical pattern of seborrhoea, a very short healing process of the skin and the elimination of the side effects discussed above.

The present invention is based on the recognition that oily greasy acne-like skin can be made symptom-free with the aid of a composition which sedates (allays) the skin, simultaneously accelerates secretion and at the same time disinfects the skin and grafually normalizes the production of sebum. In prior art no cream meeting the above requirements has been disclosed, nor has been such used in practice.

It has been found that the above object may be achieved by using compositions comprising certain plant extracts.

The present invention is based on the recognition that the rhizoma (*Graminis rhizoma*) of wheat grass (*Agropyron repens*) comprises components which may be extracted and admixed with conventional carriers and diluents used in cosmetics to yield a composition suitable for the effective treatment and healing of various forms of manifestation of acne.

According to the present invention there is provided a composition for the treatment of various forms of acne, particularly in the form of cream, tonic, soap, body hygienic composition, face packing jelly and champoon comprising in an amount of 2-95% by weight of the rhizoma (*Graminia rhizoma*) of wheat grass (*Agropyron repens*) in admixture with 5-98% by weight of additives and/or diluents generally used in cosmetics, particularly natural fats, oils, emulsifiers, conserving agents and odorants and optionally with an antibacterial agent and/or further plant extract.

According to a feature of the present invention the compositions comprise the extracts of several plants—among others that of wheat grass (*Agropyron repens*). In this case the inositol, triticine, saponine, carotine, silicic acid, malic acid, citric acid, tanning agent, vitamin and saccharide content of the compositions simultaneously exhibit the normalizing effect on the oily, greasy skin without overdrying or irritating the same.

The favorable effect of the *Graminis rhyzome* extract is due to the fact that the extract of the drogue comprises a relatively high amount of saponine which is capable already in a low doese to start the absorption of other substances by initiating secretion. The saponine content of compositions comprising the extracts of several plants may be increased by admixing the extracts of further drogues comprising saponine (e.g. the extract of *Equiseti herba*).

The compositions of the present invention suitable for the treatment and healing of bacterial infection appearing as symptoms of various forms of acne may comprise various antibiotics too. Such compositions are capable of achieving significant improvements of more serious forms of acne within a relatively short period of time. It has been found that *Graminis rhyzoma* extract and the antibiotic complement each other in a highly preferable manner.

As antibiotic penicillin, erythromycin, oxytetracyclin and neomycin may be advantageously used. Best results have been obtained by using erythromycin.

According to a further feature of the present invention there is provided a process of the preparation of a composition for the treatment of various forms of acne, particularly in the form of cream, tonic, soap, body hygienic composition, face packing jelly and champoon which comprises extracting the rhizome (*Graminis rhizoma*) of wheat grass (*Agropyron repens*/with water and/or alcohol at a temperature between room temperature and boiling point for 0.3-96 hours, and thereafter admixing the extract having a dry substance content of 0.1-7.0% by weight thus obtained with 5-98% by weight of additives and/or diluents generally used in cosmetics, particularly natural fats, oils, emulsifiers, conserving agents and odorants and optionally with an antibacterial agent and/or further plant extract in a manner known per se.

The cosmetical compositions of the present invenion are suitable for the treatment of patients suffering from acne. The compositions of the present invention comprising *Graminis rhizoma* extract may be finished in conventional forms used in cosmetics, e.g. cream, tonic, soap, body hygienic compositions, face milk, shampoo, face packing jelly etc.

Further details of the present invention are to be found in the following Examples without limiting the scope of protection to the said Examples. Examples 1-14 relate to the preparation of plant extracts. In the further Examples the preparation of various cosmetical compositions is disclosed.

EXAMPLE 1

Preparation of aqueous extract of wheat grass (*Agropyron repens*) rhizoma (*Graminis rhizoma*)

10 kg of purified and ground *Graminis rhizoma* are stirred is 100 l of hot (95° C.) water for 2 hours. The stirring having been terminated the mixture is subjected to centrifuging. The extract thus obtained is stored till further use under the exclusion of light, heat and air.

EXAMPLE 2

Preparation of an alcoholic extract of *Graminis rhizoma*

10 kg of purified and ground Graminis rhizoma are admixed with 68 l of an aqueous alcoholic solution (ethanol content 70%), the mixture is allowed to stand for 5 days and stirred several times each day. After standing the mixture is filtered and stored till further use under the exclusion of light, heat and air.

EXAMPLE 3

Preparation of an aqueous extract of the overground shoot (*Equiseti herba*) of horsetail (*Equisetum arvense* L.)

10 kg of purified and ground horsetail are stirred in hot (90° C.) water for 20 minutes. After stirring the mixture is filtered and stored till further use under the exclusion of light, heat and air.

EXAMPLE 4

Preparation of an alcoholic extract of the overground shoot of Lorsetail (*Eqiseti herba*)

One proceeds in an analoguous manner to Example 2 except that *Equiseti herba* is used as starting material.

EXAMPLE 5

Preparation of the aqueous extract of the ripe pseudocrops (*Cyanosbati pseudofructus*) of rose-hip (*Rosa caninal*)

10 kg of dried and ground rose-hips are stirred in warm (60° C.) water for 45 minutes. After stirring the mixture is filtered, a conserving agent is added and the filtrate is stored until further use under the exclusion of heat, light and air.

EXAMPLE 6

Preparation of an alcoholic extract of the ripe pseudocrops (*Cyanosbati pseudofructus*) of rose-hip (*Rosa caninal*)

One proceeds according to Example 2 except that *Cynosbati pseudofructus* is used as starting material.

EXAMPLE 7

Preparation of the aqueous extract of the composite inflorescense (*Chamomillae flos*) of camomile (Matricaria)

10 kg of dried and purified camomile flowers are stirred in 80 l of hot (80° C.) water for 10 minutes. After stirring the mixture is filtered and the filtrate is stored until further use under the exclusion of light, heat and air.

EXAMPLE 8

Preparation of the alcoholic extract of the composite inflorescence (*Chamomillae flos*) of camomile (Matricaria)

One proceeds according to process of Example 6.

EXAMPLE 9

Preparation of the aqueous extract of thyme (*Thymus serpyllum* L.) (*Thymi herba*)

10 kg of dried, purified and ground thyme are stirred in 80 l of hot (90° C.) water for 15 minutes. After stirring the mixture os filtered and the filtrate is stored till further use under the exclusion of light, heat and air.

EXAMPLE 10

Preparation of the alcoholic extract of thyme (*Thymus serpyllon*) (*Thymi herba*)

One proceeds according to process of Example 6 Pharmacopoea Hungarica.

EXAMPLE 11

Preparation of an aqueous extract of a combined drogue

A 1.0:5.0:1.5 mixture of *Equiseti herba:Cynosbati pseudofructus:Graminis rhizoma* is allowed to stand in a sevenfold amount of warm/60° C.) water for 3 days, whereupon the solution is filtered and the filtrate is stored under the exclusion of heat, light and air.

EXAMPLE 12

Preparation of an alcoholic extract of a combined drogue

A 1:2.5 mixture of *Thymi herba* and *Chamomillae flos* is ground and allowed to stand in 90% ethanol for 24 hours. The alcoholic solution is filtered and the filtrate is stored under the exclusion of heat and light.

EXAMPLE 13

Preparation of an active ingredient comprising five components of plant origin

The solution prepared according to Examples 11 and 12 are admixed in a 1:1 ratio and carriers generally used is cosmetics are added.

EXAMPLE 14

Preparation of a dry extract of *Graminis rhizoma*

An aqueous extract prepared according to Example 1 is subjected to lyophobization under aseptical conditions. The lyophobized product thus obtained is stored till further use under the exclusion of light and heat.

EXAMPLE 15

Cream for use during daytime

| Content | Amount |
| --- | --- |
| Aqueous extract of *Graminis rhizoma* | 28.0 g |
| Cetyl alcohol | 4.5 g |
| Steroic acid | 4.0 g |
| BRIJ 721 | 4.0 g |
| cosmetical white petrolatum oil | 1.5 g |
| Castor oil | 2.0 g |
| Propylene glycol | 5.0 g |
| Retinoic acid | 0.05 g |
| Ethanol (96%) | 5.0 g |
| Distilled water | 45,55 g |
| Stabilizer | 0.2 g |

| Content | Amount |
| --- | --- |
| -continued | |
| Perfume | 0.2 g |

EXAMPLE 16

Cream for use during night

| Component | Amount |
| --- | --- |
| Alcoholic extract of *Graminis rhizoma* | 0.3 g |
| Alcoholic extract of *Thymi herba* | 7.0 g |
| Alcoholic extract of *Chamomillae flos* | 6.0 g |
| Alcoholic extract of *Cynosbati pseudofructus* | 19.0 g |
| Alcoholic extract of *Equiseti herba* | 2.0 g |
| Castor oil | 3.0 g |
| Isopropyl palmitate | 5.0 g |
| Hostacerin CG | 10.0 g |
| Propylene glycol | 3.0 g |
| Distilled water, added preservative | 44.5 g |
| Perfume | 0.2 g |

EXAMPLE 17

Cream

| Component | Amount |
| --- | --- |
| Aqueous extract of *Graminis rhizoma* | 28.0 g |
| Cetyl alcohol | 6.5 g |
| Stearine | 5.4 g |
| Cosmetical white petrolatum oil | 1.5 g |
| Propylene glycol | 5.0 g |
| Sorbitol | 3.0 g |
| Sodium Lauryl sulfate | 0.5 g |
| Nipagin M | 0.2 g |
| Erythromycin base | 1.5 g |
| Ethanol (96%) | 4.0 g |
| Distilled water, added preservative | 44.2 g |
| Perfume | 0.2 g |

EXAMPLE 18

Washing emulsion

| component | Amount |
| --- | --- |
| Aqueous extract of *Graminis rhizoma* | 28.0 g |
| Aqueous extract of *Chamomillae flos* | 2.0 g |
| Aqueous extract of *Cynosbati pseudofructus* | 5.0 g |
| Hostaphat KL 340 N | 2.0 g |
| Hostacerin DGS | 4.0 g |
| Hostacerin PN 73 | 0.60 g |
| Paraffin oil | 5.0 g |
| Isopropyl palmitate | 6.0 g |
| Propylene glycol | 3.0 g |
| Distilled water, added preservative | 44.2 g |
| Perfume | 0.2 g |

EXAMPLE 19

Tonic

| component | Amount |
| --- | --- |
| Alcoholic extract of *Graminis rhizoma* | 28.0 g |
| Erythromycin base | 1.5 g |
| Ethanol (96%) | 48.5 g |
| Propylene glycol | 5.0 g |
| Distilled water | 16.8 g |
| Perfume | 0.2 g |

EXAMPLE 20

Tonic

| component | Amount |
|---|---|
| Alcoholic extract of *Graminis rhizoma* | 28.0 g |
| Retinoic acid | 0.05 g |
| Ethanol (96%) | 61.25 g |
| Propylene glycol | 10.0 g |
| Tween 20 | 0.5 g |
| Perfume | 0.2 g |

EXAMPLE 21

Soap

| Component | Amount |
|---|---|
| Dry extract of *Graminis rhizoma* | 2.0 g |
| Soap | 60.0 g |
| Hostapon T | 10.0 g |
| Sodium tripolyphosphate | 10.0 g |
| Sodium citrate | 13.0 g |

EXAMPLE 22

Liquid soap

| Component | Amount |
|---|---|
| Aqueous extract of *Graminis rhizoma* | 30.0 g |
| Aqueous extract of *Equiseti herba* | 2.0 g |
| Aqueous extract of *Cynosbati pseudofructus* | 5.0 g |
| Genapol TSM | 3.0 g |
| Genapol LRO | 35.0 g |
| Medilan KA | 8.0 g |
| Sodium chloride | 1.3 g |
| Distilled water, added preservative | 15.5 g |
| Perfume | 0.2 g |

EXAMPLE 23

Shampoo

| Component | Amount |
|---|---|
| Aqueous extract of *Graminis rhizoma* | 24.0 g |
| Aqueous extract of *Thymi herba* | 4.0 g |
| Aqueous extract of *Cynobasti pseudofructus* | 6.0 g |
| Aqueous extract of *Chamomillae flos* | 3.0 g |
| Genapol ZRO | 35.0 g |
| Genapol AMS | 10.0 g |
| Betaine | 6.0 g |
| Cocoa fetty acid diethanolamide | 2.0 g |
| Distilled water, added preservative | 6.4 g |
| Sodium chloride | 1.4 g |
| Perfume | 0.2 g |

EXAMPLE 24

Face packing jelly

| Component | Amount |
|---|---|
| Aqueous extract of *Graminis rhizoma* | 25.0 g |
| Aqueous extract of *Equiseti herba* | 10.0 g |
| Aqueous extract of *Cynosbati pseudofructus* | 5.0 g |
| Carbopol 940 | 1.0 g |
| Sodium hydroxide solution (10%) | 2.0 g |
| Distilled water, added preservative | 56.8 g |
| Perfume | 0.2 g |

EXAMPLE 25

Tonic

| Component | Amount |
|---|---|
| Erythromycin lactobionate | 2.25 g |
| Aqueous extract of *Graminis rhizoma* | 28.0 g |
| Propylene glycol | 10.0 g |
| Ethanol (96%) | 43.5 g |
| Deionized | 16.25 g | cl EXAMPLE 26

Cream for daytime use

| Component | Amount |
|---|---|
| Erythromycin lactobionate | 2.25 g |
| Aqueous extract of *Graminis rhizoma* | 28.0 g |
| Cetyl alcohol | 10.0 g |
| Brij 721 | 4.0 g |
| Carbopol 940 | 0.10 g |
| Nipagin M | 0.20 g |
| Deionized | 55.45 g |

The activity of the composition of the present invention is proved by the following clinical tests. The compositions are tested on 69 patients (43 female, 26 male), the age of the patients vary between 12 and 30 years, average age 16 years. The distribution of the various forms of acne is as follows:

| | |
|---|---|
| more serious symptoms of acne comedonics | 55 |
| most widespread papulopustolosus lesions | 25 |
| conglobed acne symptoms | 3 |

The severeness of the pathological process is designated by the following scale, based on the number of inflammation-free (open and closed comedos) and inflammation symptoms (Papules, pustules) for one half of the face:

| | |
|---|---|
| I = | less than 10 |
| II = | 11–25 |
| III = | 26–50 |
| IV = | more than 50 |

The number of the treated patients, the symptoms of acne and the degree of clinical severity are summarized in Table 1. In addition to the above data the burning, itching, flushing, peeling side-affects appearing in the form of subjective and objective complaints are disclosed too.

When using the composition according to Example 15 cases belonging to degrees II and III—predominantly acne comedonica—become symptom-free or slow significant improvement within about 8–12 weeks, while more severe cases combined with papulopustulosus lesions require further treatment. Patients showing comedo formations, papulopustulosus and conglobated symptoms belonging to degree IV require generally a treatment longer than 12 weeks.

Treatment with the cream according to Example 16 terminates mild inflammatory symptoms (diffuse erythema, a few papules) after a treatment of one or two weeks (two treatments per day). The use of this cream is suitable for both preventive and post-treatment purposes, according to experimental evidence. None of the 13 treated patients show any irritative side-effects of intolerance.

Photo-patch test treatment is carried out on 13 paquickly alleviated. On continuous treatment the number of papules gradually decrease and the oily-greasy character and comado formation abates.

TABLE 1

| Composition Example No. | Number of treated patients | | comedonica | | | | acne pop. pustulosa | | | | conglobata | | result | | |
|---|---|---|---|---|---|---|---|---|---|---|---|---|---|---|---|
| | Female | Male | I | II | III | IV | I | II | III | IV | I | II | recovered | improved | no change |
| 15 | 8 | 5 | | 2 | 4 | 6 | 1 | 8 | 2 | 1 | | 2 | 2 | 11 | — |
| 17 | 11 | 6 | | 2 | 11 | 4 | 1 | 6 | 8 | 2 | | | 5 | 12 | — |
| 18 | 11 | 1 | 1 | 6 | 4 | | 2 | 7 | | | | 1 | 6 | 6 | — |
| 19 | 5 | 9 | | | 9 | 5 | | 5 | 8 | 1 | | | 1 | 13 | — |
| 20 | 8 | 5 | | 1 | 9 | 3 | 1 | 6 | 3 | | | | 6 | 7 | — |
| 25 | 7 | 2 | 2 | 1 | 2 | | 1 | 1 | 2 | | | | 3 | 6 | — |
| | 50 | 28 | 3 | 12 | 39 | 18 | 6 | 33 | 23 | 4 | | 3 | 23 | 55 | — | tients and 8 controls. The average age of the patients is 13.5 years (12–18 years; 2 male and 11 female patients). Nine patients suffer from acne comedonica and 4 patients from acne populopustulus. The epicutane administered substance is removed after 24 hour whereupon the test extremity and contralateral control member are irradiated with an energy of 5 J/cm$^2$ for 20 minutes each. It has been found in the photo patch test that none of the 13 treated patients and the controls show any irritative or early or late-stage allergic reaction and none of the patients complained for any side-effects.

The compositions according to Example 25 is tested on 9 patient. Particularly the face and sometimes the back, shoulders and chest are treated. The affected surfaces are carefully cleaned (with warm soap water). The test composition is used twice a day at the beginning and once a day after 10 days. In each case improvement is observed. The results are most striking in the case of more severe forms of acne. In the case of seborrhoeal oily greasy skin the redness of the face and itching are mitigated and the inflammatory symptoms cease. In the case of more severe papulopustulosus lesions the subjective complaints (burning itching feeling) are

What we claim is:

1. Composition for the treatment of various forms of acne, comprising in an amount of 2%–95% by weight the rhizoma (*Graminia rhizoma*) of wheat grass (*Agropyron repens*) in admixture with 5%–98% by weight of cosmetically acceptable additives and/or diluents and with or without an antibacterial agent and/or further a plant extract.

2. The composition of claim 1, wherein the antibacterial agent is erythromycin in an amount of 0.2%–6% by weight.

3. The composition of claim 1, wherein the plant extract is *Cynosbati pseudofructus, Equiseti herba, Thymi herba* and/or *Chamomillas flos*.

4. The composition of claim 1, wherein it is in the form of a cream, tonic, soap, body hygienic, face packing jelly, or shampoo.

5. The composition of claim 1, wherein the additives and/or diluents are natural fats, oils, emulsifiers, conserving agents, and odorants.

6. The composition of claim 2, wherein the erythromycin is erythromycin lactate.

* * * * *

UNITED STATES PATENT AND TRADEMARK OFFICE
CERTIFICATE OF CORRECTION

PATENT NO. : 4,803,069
DATED : February 7, 1989
INVENTOR(S) : Sándor Kékesi et al.

It is certified that error appears in the above-identified patent and that said Letters Patent is hereby corrected as shown below:

ON THE TITLE PAGE,
The correct filing date of the application is June 13, 1986.

Signed and Sealed this

Twenty-first Day of November, 1989

Attest:

JEFFREY M. SAMUELS

*Attesting Officer*   *Acting Commissioner of Patents and Trademarks*